United States Patent [19]

Shields et al.

[11] Patent Number: 5,740,943
[45] Date of Patent: Apr. 21, 1998

[54] STERILE BIASED COT AND EXAMINATION GLOVE DISPENSERS

[76] Inventors: Jack W. Shields, 1950 Las Tunas Rd., Santa Barbara, Calif. 93103; W. Mark Shields, 1735 Clearview Rd., Santa Barbara, Calif. 93101

[21] Appl. No.: 812,963

[22] Filed: Mar. 5, 1997

[51] Int. Cl.[6] .................................................. B65H 1/00
[52] U.S. Cl. ............................................. 221/33; 206/438
[58] Field of Search ................................. 221/33, 31, 30, 221/26; 206/438, 476, 822, 828, 804, 812

[56] References Cited

U.S. PATENT DOCUMENTS 4,131,195  12/1978  Worrell, Sr. ........................ 206/812
5,044,494   9/1991  Tamara ............................... 206/438

*Primary Examiner*—Kenneth Noland

[57] ABSTRACT

We disclose dispensers for sterile finger cots without rolled bases, but having biased bases; and for sterile conventional examination gloves having short cuffs with beaded rolled bases. The invention enables users to extract each cot and each glove from a sterile sealed envelope without contaminating the leading external portions of any finger cot or any glove; and enables easy removal of each finger cot or glove without the user touching any likely-to-be contaminated external surface by any finger after appropriate use. Such dispensers for finger cots and gloves can supply multiples, each enclosed in a a sealed envelope which manually opens to expose only the biased base of each contained cot or opens on a bias which exposes only the beaded rolled base and proximal part of each short glove cuff. The object is to sustain the highest level of sterility conveniently possible during the use of gloves or finger cots for protecting patients and users from cross-infections.

4 Claims, 2 Drawing Sheets

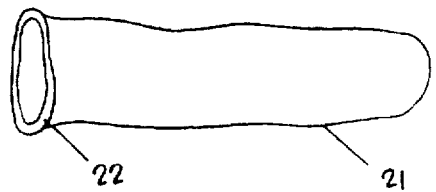
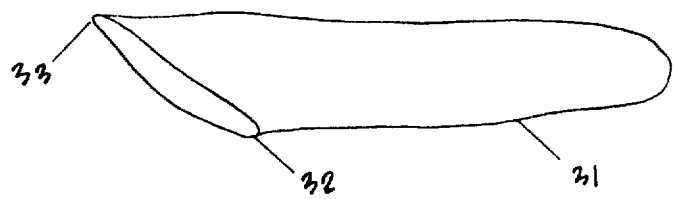
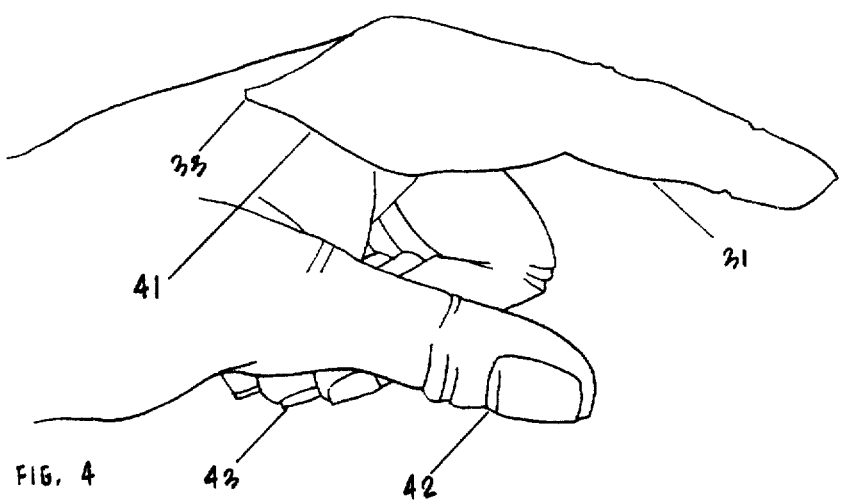
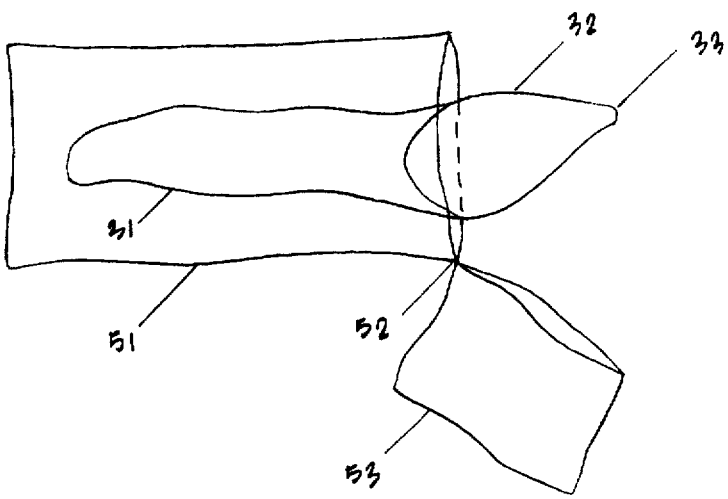

STERILE BIASED COT AND EXAMINATION GLOVE DISPENSERS

FIELD OF THE INVENTION

This invention relates to the stale dispensation of finger cots with biased bases and examination gloves with short beaded cuffs to minimize bacterial or vital cross-infections between patients and users in health care settings, especially when guiding the insertion of needles into veins under the skin, palpation of abscesses or tumors under apparently inflamed skin or mucous membranes, and various other purposes where a single gloved finger or one gloved hand is needed for medical or dental purposes.

DESCRIPTION OF THE PRIOR ART

Since the issuance of Universal Precautions for preventing the transmission of bloodborne pathogens in 1987, health care workers have become accustomed to using unsterile examination gloves for protecting themselves when performing a variety of procedures on patients. Such examination gloves are mostly made from latex in S-E Asia, and are packaged at random without sterilization in boxes containing a pound or 100 gloves. They differ from sterile surgical gloves in that each glove, lacking a thumb apposed toward the palm, fits either hand; and the cuffs, instead of being long and folded over the palms, are short with a beaded proximal end made of tightly rolled glove material, either latex or synthetic. The external surfaces of such examination gloves are not sterile to begin with. When successively grasped by fingers from a box for donning, randomly presenting parts, usually fingers or a thumb, cuffs and palms present in this order of decreasing frequency. The beads on the cuffs present occasionally, but less than 30% of the time and seldom can be grasped without touching another part of the glove, the next glove or several gloves sticking together in a bunch. The potential for user contamination of each glove is compounded by the facts that (a) statistical studies in medical and dental health care settings reveal only 20–40% of health care workers wash their hands immediately before donning a an examination glove or a pair; and (b) a pair lacking long cuff over palm overfolds cannot be put on without touching the external surfaces of both gloves, first, with bare hands and, later, with two potentially contaminated gloved hands, obliged to mutually adjust the glove comfortably and usefully onto the fingers and wrists of each hand. Each glove is subject to further, as well cumulative external contamination, the longer each glove or pair is worn. The last becomes significant when statistics in medical and dental health care settings indicate that the same glove or pair is used on more than one patient, at least 50% of the times a pair was put on. Thus, the use of a dispenser for an easily accessed single sterile examination glove which can be donned without contaminating the fingers, thumb or palms would seem desirable, especially if the glove were to be used for a single purpose on a given patient.

With respect to finger cots, usage has decreased somewhat proportional to increased examination glove usage since 1987. However, finger cots are extremely useful for purposes wherein palpation with one finger is sufficient during the insertion of a needle into a vein, feeling over mucous membranes or skin, or feeling open wounds for relevant pathology or foreign material. Currently, as shown in Sheet 1 of the drawings, finger cots are made to fit a single finger, usually the index finger of either hand. They are made by molding, usually from latex, with a proximal bead over which the entire cot is rolled such that the user can put the cot on a selected finger by unrolling the cot proximally, using the index finger and thumb of the other hand. After use for an intended purpose, the finger cot is rolled forward over the bead by means of fingers of the other hand until the cot assumes the original rolled configuration. As results, the beaded and rolled finger cot cannot be put on sterile, unless the other hand is sterile or fitted with a sterile surgical glove. Thus, finger cots are not supplied sterile individually, or sterile in unsterile boxes dispensing 100 successively, and grasped at random. They are still frequently used in sterile operating rooms after removal from such boxes, and autoclave sterilization of desired numbers dispensed in sterile packages. Therefore, the use of a finger cot applicable sterile for selected procedures, and removable without contaminating fingers of the other hand might prove beneficial for patients, as well as for health care workers.

A computerized patent search through cogent U.S. patent abstracts 1950 to November 1996 via IFI/Plenum Data Corporation on Feb. 10, 1997 reveals no finger cots supplied sterile, or in sterile containers; and none with the finger bases cut on the bias, thus eliminating the proximally rolled beads and the rolling off and rolling on of finger cots. Small entity provisional U.S. patent application 60/012,802, filed Mar. 4, 1996 for "Over-Folded Sterile Glove Dispensers", summarizes and discloses the effective prior use of sterile surgical gloves with long cuff over palm overfolds, as opposed to the current use of unsterile examination gloves. In this co-pending patent, the overfolding of examination glove cuffs over palms was disclosed as a means to dispense examination gloves in sterile condition such that examination gloves could be put on sterile singly or in pairs conveniently by standard unassisted gloving procedure. In addition, sealed sterile envelope dispensers for examination gloves with short beaded cuffs were disclosed and claimed. The instant patent application differs from the previously fried co-patent in that the sealed envelopes are disclosed to open on a bias, such that tearing to open the end of the envelope containing the cuff is more likely to expose only the bead and proximal part of the cuff, such that the user, preferably with washed hands, can conveniently glove one hand or the other without touching the fingers, thumbs or palms. However, if both hands are to be gloved with examination gloves by standard unassisted glove procedure, it is still essential that each glove is supplied with a long cuff over palm overfold, such that the fingers of one hand can slide under the overfold to sterile glove the other.

The finger cot application of the invention disclosed herein is essentially a bias cut in the base of an index finger part of a sterile glove, such that a users' index finger can be easily inserted after removal from a convenient sterile dispenser; and can be easily removed from the finger after glove use. The examination glove application disclosed herein differs only in that the sterile sealed envelope containing a conventional examination glove is designed to open across the cuff-containing end on a bias, instead of straight across.

We hope these disclosures will improve the usage of gloves commonly employed in medical and dental care in the best interests of patients, as well health care workers also needing protection from blood-borne, skin-borne and glove-borne born microorganisms.

BRIEF DESCRIPTION OF THE DRAWINGS

FIG. 1 shows a conventional rolled finger cot.

FIG. 2 shows a finger cot conventionally unrolled.

3

FIG. 3 shows a finger cot with a biased, instead of a rolled base.

FIG. 4 shows a biased finger cot applied to an index finger.

FIG. 5 shows a sealed envelope which opens transversely to expose the bias on the finger cot.

Figure 6:
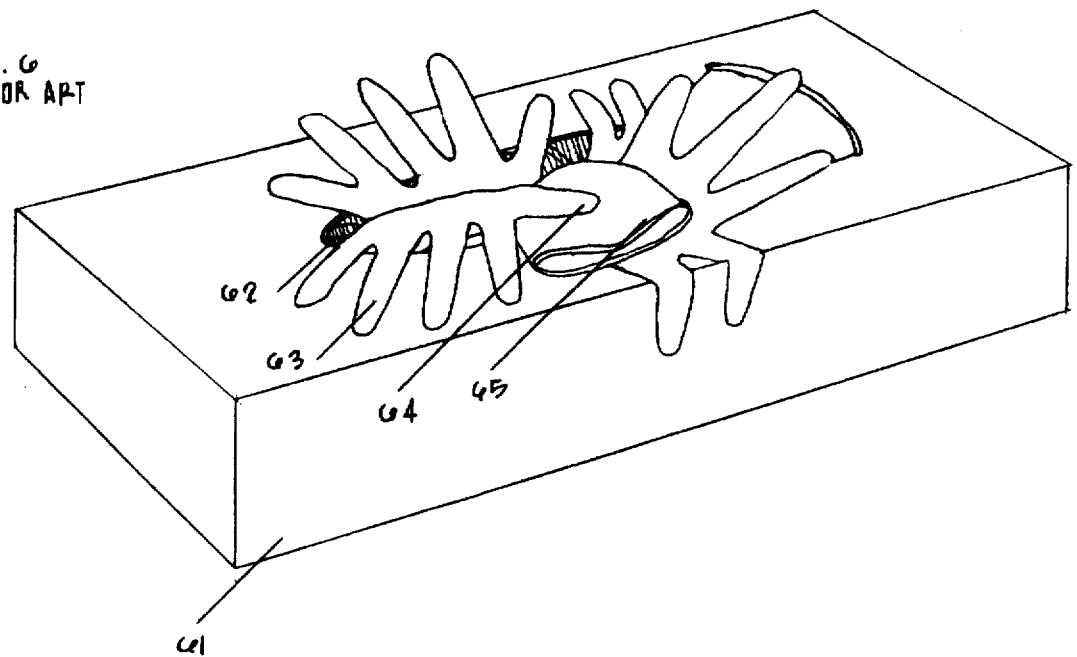

FIG. 6 shows the random presentation of examination glove parts from an unsterile box originally containing 100.

Figure 7:
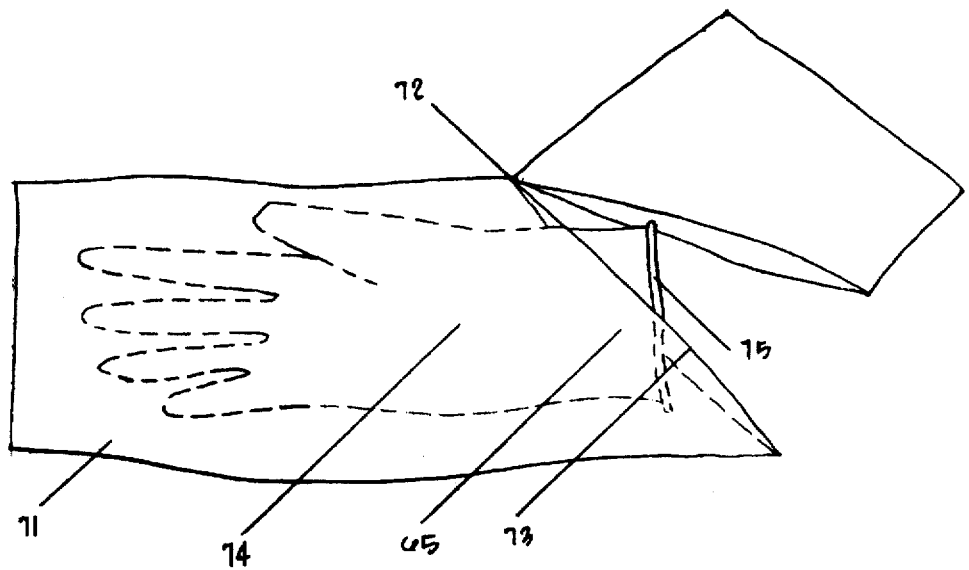

FIG. 7 shows a conventional examination glove in a sterile envelope which tears open on a bias most likely to expose only the bead and proximal part of an examination glove for finger grasping.

DESCRIPTION OF THE PREFERRED EMBODIMENTS

FIG. 1 (Prior art) shows a rolled finger cot 11, as currently supplied unsterile.

FIG. 2 (Prior art) shows the extension of the finger cot 21 from the roll 22, such that the cot can be stretched over a finger for intended uses. With repetitive testing over an inserted finger, it will be found impossible to unroll the cot backward over the inserted finger by means of the thumb and forefinger of the other hand without contaminating the leading end of the cot. Rolling the cot forward off the finger after use, such that the fingers of the opposite hand do not touch the leading end of the cot will be found almost equally difficult, partly because the thumb and index finger of the opposite hand have so little to grasp.

FIG. 3 shows a finger cot 31 with a biased base 32 wherein the apex of the bias 33 extends backwards far beyond the leading cut of the bias 32.

FIG. 4 shows how the basally biased cot 31 fits over an extended index finger 41 of a left hand whose thumb 42 and remaining fingers 43 are flexed out of the way. It should be noted that the apex 33 of the bias 32 extends backward over the dorsum of the hand and base of the index finger, such that it is easily grasped by fingers of the opposite hand for removal, as well as putting on the cot.

FIG. 5 shows how such finger cots 31 can be enveloped in packages 51 which manually tear apart 52 at appropriate sites 53 to expose only the apex 33 of the bias 32 for finger grasping by means of the thumb and index finger of the users' other hand.

Not illustrated here, but shown in Provisional U.S. patent application 60/012,802, such envelopes can be dispensed in specified numbers in sterile boxes or in rolls of envelopes which deliver one sterile finger cot after another.

For use in guiding the insertion of hollow-bore needles employed for phlebotomy or giving intravenous infusions, health care workers should:

1. Routinely sterile-prep the skin over an intended venipuncture site, after organizing all the sterile paraphernalia essential to venipuncture.

2. As the last maneuver just before inserting the essential hollow needle through the skin, use the thumb and forefinger of the dominant hand to rip off the end of the dispenser envelope 51 to expose the apex 33 and biased base 32 of the finger cot.

3. With the dominant hand, gasp the apex 33 and exposed portion and biased crease 32 of the finger cot 31 to remove the cot from the sterile envelope; and, in turn, continue to grasp the apex between 33 and 32 for gloving the index finger of the non-dominant hand in a direction most remote from the thumb, fingers and knuckle of dominant hand.

4. Use the sterile-gloved forefinger of the non-dominant hand for feeling over the sterile-prepped prospective venipuncture site to help guide the accurate intravenous insertion of the chosen hollow-bore needle 5. When the hollow needle is accurately placed, the user will not take the cot off, but leave it on to help manipulate Vacutainer tubes and holders in the case of phlebotomy, or attach trailing tubing in the case of IV infusion.

6. In the case of phlebotomy, after the venous blood is withdrawn and it's time to withdraw the needle, the cotted finger will be used to pick up a sterile pledget, preferably one whose size is about the same as a finger tip and has an upper surface which will adhere to the tip of the finger cot, such that the finger tip can be used to maintain pressure over the venipuncture site.

7. Finger pressure will then be exerted over the venipuncture site while the hollow needle is withdrawn and maintained for as long as takes to prevent venous injury and optimally control venous bleeding; and until the dominant hand becomes free after safe disposal of the hollow needle, along with the paraphernalia to which the needle is attached.

8. After all conditions in step 7 are satisfied, the thumb and forefinger of the dominant hand will be used to remove the finger cot from the non-dominant hand by grasping the apex of the to slip the cot off the index finger and, simultaneously, turn the cot inside out, such that the adherent pledget and the inverted cot can be disposed of safely and together.

In the case of I.V. infusions wherein the hollow needle is left in place for hours, the cot will be removed, as outlined in step 8, as soon as the dominant hand becomes free. When it's time to remove the needle, another sterile finger cot will be used similarly with or without an adherent pledget.

In the case of finger cot use for feeling over inflamed skin for an underlying abscess or tumor, the cot might be put on, as described in steps 2–3; but put on the index finger of the dominant hand. Again, the cot should be inverted during removal, as described in step 8, so that external surfaces contaminated with blood or microorganisms will be on the inside, as soon as finger cot is removed.

In the case of using sterile finger cots for picking up objects which are sterile, or picking up and rapidly disposing of objects which are not sterile, two sterile envelopes should be opened to expose the biases bases on two cots, such that the index finger and thumb of one hand can be covered in succession without touching the leading end of either cot.

FIG. 6 shows a box 61 having an ovoid opening 62 through which unsterile examination gloves are manually grasped one after another. It will be noted that the presentation of fingers 63, thumbs 64, and cuffs 65 are random. Therefore, contamination by bare fingers and thumbs used to extract each glove can be expected to be random, especially if the user has to manipulate each glove to grasp the bead on a short cuff over palm fold to insert the other hand inside a glove. If two gloves are put on in succession, the problem may be compounded by using contaminated parts of each glove to help put on the other and, then, use both hands to adjust the fingers and cuffs to each hand.

FIG. 7 shows a sealed sterile envelope 71 whose tearing off 72 on a bias 73 over the cuff 65 of a contained sterile examination glove 74 will uniformly allow the first and second fingers of a grasping hand to grasp the rolled bead 75 and proximal part of the cuff 65, such that the contained glove can be donned without touching the fingers, thumb or palm. The sterile gloved hand may be used for whatever medical or dental purpose which can be accomplished with one hand. After the intended use, the ungloved hand can grasp the rolled bead 75 and proximal part of the cuff 65 to unglove the gloved hand by turning the glove inside out such that the fingers, thumb and palm are not touched or likely to touch any other object before appropriate disposition.

Not illustrated here, but shown in Provisional U.S. patent application 60/012,802, and in the corresponding patent applied for, such sealed sterile envelopes can be dispensed in specified numbers in sterile boxes or in rolls of sealed envelopes which deliver one sterile examination glove after another. Use of the sterile examination glove after manual extraction from the dispenser and donning the glove without touching the fingers, thumbs or palms should be as described previously for sterile fingers cots with biased bases. However, because the entire hand is gloved, usage can be expected to be more versatile for palpating inside the mouth, vagina, rectum or over large areas of skin. Again, it should be emphasized that single use of each glove for a given purpose, along with careful handwashing and proper fingernail trimming are essential. After the glove is used and turned inside out, appropriate disposition and washing hands again is essential to optimal patient care and care for the user's hands.

Finally, it should be added that each box or roll containing multiple sterile sealed envelopes, if the contained finger cots or examination gloves are to be used in surgical operating rooms, should be supplied with a hermetically sealed protective cover such that given numbers of externally sterile sealed envelopes can be supplied directly to the field of surgical operation.

These specifications for biased finger cots and sterile sealed envelopes for dispensing single cots and single examination gloves with beaded cuffs are primarily designed to prevent biohazardous cross-contamination between users and patients. Those familiar with the art should recognize that the specifications are exemplary and that modifications are possible without departing from the spirit of of the invention.

Therefore, we claim:

1. Sterile finger cots having biased bases with proximal apices thereon and having distal parts for covering the phalanges of a chosen finger, said proximal apices, when grasped by fingers of the opposite hand, enabling users to slip each sterile finger cot onto said chosen finger before intended use, and to invert each cot from said chosen finger after use, without touching the external surfaces of said distal parts with fingers of either hand.

2. Sterile dispensers for sterile finger cots, said sterile dispensers comprising sealed sterile envelopes whose manual opening across both sides of one end exposes only proximal apices of biased bases of said sterile finger cots for grasping by fingers of the hand opposite to the hand having said chosen finger, such that distal parts for covering the phalanges of said chosen finger are not touched by any finger or any external part of said sealed sterile envelopes during withdrawal of said sterile finger cots from said sterile dispensers.

3. Sterile dispensers, as in claim 2, applicable for dispensing sterile gloves having rolled beads on the proximal parts of the cuffs of each glove and having distal means for covering the palm and five fingers of one hand, said sterile dispensers further comprising said sealed sterile envelopes whose manual opening on a bias across both sides of one end exposes only said rolled beads and said proximal parts of the cuffs of each sterile glove for finger grasping, such that said distal means for covering the palm and five fingers of one hand are not touched by any finger or by any external parts of said sealed sterile envelopes during withdrawal of said sterile gloves from said sterile dispensers.

4. Said sterile dispensers, as in claims 2 and 3, further comprising said sealed sterile envelopes packaged in and conveniently separable from rolls.

* * * * *